United States Patent

Hanai et al.

[11] Patent Number: 5,939,280
[45] Date of Patent: Aug. 17, 1999

[54] IMMUNOLOGICAL ASSAY FOR QUANTIFYING PEG-MODIFIED HUMAN GRANULOCYTE COLONY STIMULATING FACTOR AND MONOCLONAL ANTIBODIES USED IN THE ASSAY

[75] Inventors: Nobuo Hanai, Kanagawa; Akiko Furuya; Motoo Yamasaki, both of Tokyo; Satoshi Kobayashi; Takashi Kuwabara, both of Shizuoka, all of Japan

[73] Assignee: Kyowa Hakko Kogyo Co., Ltd., Tokyo, Japan

[21] Appl. No.: 08/570,943

[22] Filed: Dec. 12, 1995

[30] Foreign Application Priority Data

Dec. 15, 1994 [JP] Japan .......................... P.HEI.6-311763

[51] Int. Cl.$^6$ ........................ G01N 33/53; G01N 33/537; G01N 33/543
[52] U.S. Cl. .................... 435/7.94; 435/7.92; 435/70.21; 435/240.27; 436/518; 436/548
[58] Field of Search ................................. 435/7.92, 7.93, 435/7.94, 7.95, 70.21, 240.27; 436/518, 548

[56] References Cited

U.S. PATENT DOCUMENTS

| | | | |
|---|---|---|---|
| 4,179,337 | 12/1979 | Davis et al. | 435/181 |
| 4,778,752 | 10/1988 | Curtiss et al. | 435/7 |
| 5,183,660 | 2/1993 | Ikeda et al. | 424/94.3 |
| 5,194,592 | 3/1993 | Yoshida | 530/388.23 |
| 5,214,132 | 5/1993 | Kuga et al. | 530/351 |
| 5,362,853 | 11/1994 | Kuga et al. | 530/351 |
| 5,414,089 | 5/1995 | Ebashi et al. | 546/243 |
| 5,529,915 | 6/1996 | Phillips et al. | 435/188 |
| 5,536,382 | 7/1996 | Sunzeri | 204/451 |
| 5,552,286 | 9/1996 | Chang et al. | 435/7.2 |
| 5,581,476 | 12/1996 | Osslund | 364/496 |
| 5,593,666 | 1/1997 | McDonald | 424/85.1 |
| 5,605,976 | 2/1997 | Martinez et al. | 525/408 |

FOREIGN PATENT DOCUMENTS

| | | |
|---|---|---|
| 0 331 186 | 9/1989 | European Pat. Off. . |
| 0401384 | 12/1990 | European Pat. Off. . |
| 0331186 | 6/1989 | United Kingdom ............ C12P 21/00 |
| 9420069 | 9/1994 | WIPO . |
| WP 94/20069 | 9/1994 | WIPO . |

OTHER PUBLICATIONS

Wadhwa, M. et al. "Production of polycolonal and monoclonal antibodies . . . " Journal of Immunological Methods. 128 (1990), pp. 211–217.

H. Yoshida et al. "Generation and characterization of monoclonal antibodies to recombinant human . . . " Agric. Biol. Chem. 53, (1989), pp. 1095–1101.

James C. Yang et al. "Murine studies using polyethylene glycol–modified . . . " Mphokine and Cytokine Research, Jun. 10, No. 6, 1991, pp. 475–480.

J.E. Layton et al. "Identification of a functional domain of human granulocyte . . . " The Journal of Biological Chemistry, 1991, The American Chemical Society for Biochemistry and Molecular Biology, Inc. vol. 266, No. 35, Dec. 15, 1991, pp. 23815–23823.

(List continued on next page.)

Primary Examiner—James C. Housel
Assistant Examiner—Ginny Allen Portner
Attorney, Agent, or Firm—Nixon & Vanderhye, P.C.

[57] ABSTRACT

An immunological assay for quantifying PEG-modified human granulocyte colony stimulating factor or derivatives thereof in a sample comprising bringing into contact with said sample an antibody which reacts with the human granulocyte colony stimulating factor or its derivative and with PEG-modified human granulocyte colony stimulating factor or its derivative and a monoclonal antibody which reacts specifically with the human granulocyte colony stimulating factor or its derivative but not with the PEG-modified human granulocyte-colony stimulating factor or its derivative.

9 Claims, 8 Drawing Sheets

OTHER PUBLICATIONS

Yoshida et al Agric. Biol. Chem 53 (4) 1095–1101, 1989 Generation and Characterization of Monoclonal Antibodies to Recombinant Human Granulocyte–colony Stimulating Factor (G–CSF) and Its Muteins.

Yamasaki et al J. Biochem. 115, 814–819 (1994) "Modification of Recombinant Human Granulocyte Colony Stimulating Factor (rhG–CSF) and Its Derivative ND 28 with Polyethylene Glycol".

Patent Abstracts of Japan vol. 012, No. 458 (p.–794), Dec. 1988 & JP–A–63 180860 Date Considered.

Database WPI Section Ch, Week 9324 Derwent Class B04, AN 93–190703 & JP–A–05 115 197.

Omori et al. "Measurement of Human G–CSF by Enzyme–Linked Immunosorbent Assay Using Monoclonal Antibody", Research in Exp. Methods (1989) 189: pp. 163–171.

Shimamura et al. Establishment of Specific Monoclonal Antibodies Against Recombinant Huan Granulocyte Colony–Stimulating Factor (hg–CSF) adn Their Application For Immunoperoxidase Staining of Paraffin–Embedded Sections. The Journal of Histochem and Cytochem vol. 38 No. 2 pp. 283–286, 1990.

Nucci, ML et al, Advanced Drug Delivery Reviews, vol. 6; pp. 133–151; 1991.

Yoshida, H et al, (1989), Agric. Biol. Chem., vol. 53, pp. 1095–1101.

Layton, JE et al, The J Biolog. Chem., 1991, vol. 266, No. 35, pp. 23815–23823, Dec. 15, 1991.

Niven, RW et al, J. Controlled Release, vol. 32, 1994, pp. 177–189.

Yamasaki, M. et al, J. Biochem, May 1994, vol. 115 No. 5, pp. 814–819.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 175 amino acids
       (B) TYPE: amino acid
       (C) STRANDEDNESS: single
       (D) TOPOLOGY: linear    (ii) MOLECULE TYPE: protein    (v) FRAGMENT TYPE: N-terminal    (vi) ORIGINAL SOURCE:
       (A) ORGANISM: Homo sapiens    (ix) FEATURE:
       (A) NAME/KEY: Modified-site
       (B) LOCATION: 0
       (D) OTHER INFORMATION:/product= "OTHER"
          /note= "X is H or Met."

(ix) FEATURE:
       (A) NAME/KEY: Protein
       (B) LOCATION: 1..174
       (D) OTHER INFORMATION:/product= "OTHER"
          /note= "human graulocyte colony stimulating factor"

(x) PUBLICATION INFORMATION:
       (H) DOCUMENT NUMBER: US 5,214,132 A
       (I) FILING DATE: 12-APR-1989
       (J) PUBLICATION DATE: 25-MAY-1993
       (K) RELEVANT RESIDUES IN SEQ ID NO:1: FROM 1 TO 175

(xi) SEQUENCE DESCRIPTION: SEQ ID NO:1:

```
Xaa Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu His
65                  70                  75

Ser Gly Leu Phe Leu Tyr Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Arg Arg Ala Gly Gly Val Leu Val Ala Ser His Leu Gln Ser
            145                 150                 155

Phe Leu Glu Val Ser Tyr Arg Val Leu Arg His Leu Ala Gln Pro
160                 165                 170
```

IMMUNOLOGICAL ASSAY FOR QUANTIFYING PEG-MODIFIED HUMAN GRANULOCYTE COLONY STIMULATING FACTOR AND MONOCLONAL ANTIBODIES USED IN THE ASSAY

FIELD OF THE INVENTION

The present invention relates to an immunological assay for quantifying polyethylene glycol-modified human granulocyte colony stimulating factor (hereinafter referred to as PEG-modified G-CSF) or derivatives thereof and monoclonal antibodies used in this method.

BACKGROUND OF THE INVENTION

PEG-modified G-CSF and PEG-modified human granulocyte colony stimulating factor derivative ND28 [JP-A-316400/89 (the term "JP-A" used herein means a published unexamined Japanese Patent Application.) corresponding to European Patent No. 0335423, WO090/06952; hereinafter referred to as PEG-modified ND28] have advantageous properties such as a longer half life in blood when compared with human granulocyte colony stimulating factor (U.S. Pat. No. 4,883,127; hereinafter referred to as G-CSF) and human granulocyte colony stimulating factor derivative ND28 (JP-A-267292/88 corresponding to European Patent No. 0272703; hereinafter referred to as ND28), and thus have high clinical efficacy. In order to use PEG-modified G-CSF and PEG-modified ND28 clinically, a specific quantification system using an antibody is necessary in order to ascertain the pharmacokinetics in blood. However, the PEG-modified molecule is not readily recognized by the immune mechanism of a host, making it difficult to construct an antibody to it [LYMPHOKINE AND CYTOKINE RESEARCH, 10, 475–480 (1990)]. Although monoclonal antibodies against G-CSF and ND28 have been obtained [anti G-CSF monoclonal antibody: JP-A-180860/88, J. Immunol. Methods, 128(2), 211–217 (1990), J. Biol. Chem., 266(35), 23815–23823, anti ND28 monoclonal antibody: JP-A-225495/89 corresponding to European Patent No. 0331186, Agric. Biol. Chem., 53, 1095–1101 (1989)], to date no antibodies which react with PEG-modified G-CSF or PEG-modified ND28 have been obtained.

SUMMARY OF THE INVENTION

An objective of this invention is to construct a monoclonal antibody which reacts with G-CSF or its derivative and PEG-modified G-CSF or its derivative and to provide an immunological assay for quantifying PEG-modified G-CSF or derivatives thereof using the monoclonal antibody.

DETAILED DESCRIPTION OF THE INVENTION

The present invention relates to an immunological assay for quantifying PEG-modified G-CSF or derivatives thereof in a sample comprising bringing into contact with said sample an antibody which reacts with G-CSF or its derivative and with PEG-modified G-CSF or its derivative and a monoclonal antibody which reacts specifically with G-CSF or its derivative but not with PEG-modified G-CSF or its derivative.

G-CSF has the amino acid sequence shown in SEQ ID NO:1. G-CSF derivatives used in the present invention is a polypeptide available upon replacement of at least one amino acid residue of the amino acid sequence shown in SEQ ID NO:1 with another kind of amino acid, e.g., the G-CSF derivatives shown in Table 1 below or a polypeptide deficient in 1 to 11 amino acid residues at the N-terminus of the amino acid sequence shown in SEQ ID NO:1. Aside from the above polypeptides, the G-CSF derivatives described in EP-A-0243153, EP-A-0237545 and WO-A-8701132 can also be used. Among them, ND28 is a polypeptide in which the 1st, 3rd, 4th, 5th and 17th amino acids in the amino acid sequence of G-CSF are replaced by alanine (Ala), threonine (Thr), tyrosine (Tyr), arginine (Arg) and serine (Ser), respectively.

TABLE 1

| Position of substitution (amino acid of G-CSF) | G-CSF derivatives | | | | | | | | | | |
|---|---|---|---|---|---|---|---|---|---|---|---|
| | a | b | c | d | e | f | g | h | i | j | k |
| Position-1 (Thr) | * | Val | Cys | Tyr | Arg | * | Asn | Ile | Ser | * | Ala |
| Position-3 (Leu) | Glu | Ile | Ile | Ile | Thr | Thr | Glu | Thr | Thr | * | Thr |
| Position-4 (Gly) | Lys | Arg | Arg | Arg | Arg | Arg | Arg | Arg | Arg | Arg | Tyr |
| Position-5 (Pro) | Ser | Ser | Ser | Ser | Ser | Ser | Ser | Ser | Ser | * | Arg |
| Position-17 (Cys) | Ser | Ser | Ser | Ser | Ser | Ser | Ser | Ser | Ser | Ser | Ser |

*No substitution

The molecular weight of PEG employed in the present invention is not particularly limited, and usually from 300 to 30,000, preferably from 1,000 to 20,000. The method of PEG modification may be any of those known in the prior art [for example, see JP-A-316400/89 corresponding to European Patent No. 0335423, Biotech. Lett., 14, 559–564 (1992), Bio/technology, 8, 343–346 (1990)].

The PEG molecule binds to amino, carboxyl, mercapto or guanidino groups of the G-CSF molecule or G-CSF derivative molecule. PEG-modified G-CSF or PEG-modified G-CSF derivative usually has from 1 to 5 molecules of PEG. The PEG-modified G-CSF or PEG-modified G-CSF derivatives in the present invention usually have the same number of PEG molecules collected by separation, or a mixture of those having different numbers of PEG molecules may be employed without separation.

The antibody which reacts with G-CSF, its derivative, PEG-modified G-CSF and its derivative according to the present invention (hereinafter referred to as antibody A) may be either a polyclonal antibody or monoclonal antibody. Examples of antibody A are rabbit anti-ND28 antibody produced as described below as well as monoclonal antibody KM509 produced by hybridoma cell line KM509. Hybridoma cell line KM509 was deposited under the Budapest Treaty with National Institute of Bioscience and Human-Technology, Agency of Industrial Science and Technology in Japan since Aug. 9, 1994 under FERM BP-4774.

An example of the monoclonal antibody which reacts specifically with G-CSF derivative but not with PEG-modified G-CSF and its derivative according to the present invention (hereinafter referred to as antibody C) is monoclonal antibody KM511produced by hybridoma cell line KM511, which reacts specifically with ND28 but not with PEG-modified G-CSF or PEG-modified ND28. An example of the monoclonal antibody which reacts specifically with G-CSF but not with PEG-modified G-CSF, its derivative and a G-CSF derivative (hereinafter referred to as antibody B) is monoclonal antibody KM343 produced by hybridoma cell line KM343, which reacts specifically with G-CSF but not with PEG-modified G-CSF or PEG-modified ND28. Hybridoma cell lines KM511 and KM343 were deposited under the Budapest Treaty with National Institute of Bioscience and Human-Technology, Agency of Industrial Science and Technology in Japan since Nov. 10, 1994 under FERM BP-4880 and FERM BP-4879, respectively.

The immunological assay employed in the present invention may be a radioimmunoassay using the solid-phase sandwich method or enzyme-linked immunosorbent assay (ELISA).

The present invention is further described below.

In the method of quantifying PEG-modified G-CSF or derivatives thereof according to the present invention, a quantification system (quantification system 1) of PEG-modified G-CSF or its derivative by an immunological assay employing an antibody (antibody A) which reacts with G-CSF, its derivative, PEG-modified G-CSF and its derivative, a quantification system specific to G-CSF (quantification system 2) employing an antibody (antibody B) which reacts specifically with G-CSF but not with PEG-modified G-CSF, its derivative and a G-CSF derivative, and a quantification system specific to G-CSF (quantification system 3) employing an antibody (antibody C) which reacts specifically with a G-CSF derivative but not with PEG-modified G-CSF or its derivative are established, and the value obtained by quantification system 2 or 3 is subtracted from the value obtained by quantification system 1 to obtain the value corresponding exclusively to PEG-modified G-CSF or its derivative. The method of establishing the quantification systems in the case where ND28 is employed as a G-CSF derivative is described below.

1. Establishment of Each Quantification System (1) Establishment of quantification system for G-CSF or ND28 and PEG-modified G-CSF or PEG-modified ND28-employing antibody A.

From 1 to 50 μg/ml of antibody A as the first antibody is dispensed in a volume of 10 to 100 μl/well to 96-well microplate, which is then kept at 4° C. overnight, whereby effecting coating onto the plate. After blocking, for example, with BSA solution [PBS solution (1.83 g of disodium hydrogen phosphate, 0.21 g of potassium dihydrogen phosphate, 7.65 g of sodium chloride, 1 L of distilled water, pH 7.2) supplemented with 1% fetal bovine serum (BSA)], PEG-modified G-CSF or PEG-modified ND28, which has previously been subjected to serial dilution, is dispensed in a volume of 50 to 100 μl/well, and reacted at room temperature for 2 hours or at 4° C. overnight. After washing with PBS or PBS supplemented with 0.5% Tween-20 (PBS-Tween), 1 to 50 μg/ml solution of antibody A labelled with biotin, an enzyme, a chemiluminescent substance or a radioactive compound or the like as the second antibody is dispensed in a volume of 50 to 100 μl/well, and reacted at room temperature for 1 to 2 hours. After thorough washing, a reaction appropriate for the detectable label or the second antibody is conducted, whereby establishing the quantification system for G-CSF or ND28 and PEG-modified G-CSF and PEG-modified ND28.

(2) Establishment of quantification system for ND28 employing antibody C

The quantification system for ND28 by sandwich ELISA is established similarly as described under (1) except that antibody C is employed as the first antibody and antibody A obtained as described under (1) as the second antibody.

(3) Establishment of quantification system for G-CSF employing antibody B

The quantification system for G-CSF by sandwich ELISA is established similarly as described under (1) except that antibody B is employed as the first antibody and antibody A obtained as described under (1) as the second antibody.

The method of constructing antibody A, B and C according to the present invention in the case where ND28 is employed as a G-CSF derivative is described below.

2. Construction of Antibody A, B and C (1) Immunization of animals and preparation of antibody-producing cells Mice or rats of 3 to 20 weeks of age are immunized with G-CSF produced by *E. coli* using recombinant DNA technology, ND28 produced by *E. coli* or peptide fragments thereof, such as the peptide having the 168 to 174th amino acid sequence of ND28 with cysteine (Cys) added at the N-terminal (PEG-5), the peptide having the 59th to 70th amino acid sequence of ND28 with Cys at the 64 position being replaced with serine (Ser) and Cys being added at the N-terminal (PEG-9), and the peptide having the 92nd to 99th amino acid sequence of ND28 with Cys added at the N-terminal (PEG-10). To enhance immunogenicity, the peptide fragments derived from ND28 are conjugated with hemocyanine keyhole limpet (hereinafter referred to as KLH) or bovine serum albumin (BSA) when used in the immunization. The immunization of the animals is performed by subcutaneous, intravenous or intraperitoneal administration using a suitable adjuvant [for example, complete Freund's adjuvant or aluminum hydroxide gel with pertussis vaccine]. The immunogens are administered repetitively 5 to 10 times at an interval of 1 to 2 weeks after the first administration. Three to seven days after each administration, blood sample is taken from venous plexus of the fundus of the eye, and the serum derived from the sample blood is examined for reactivity with the immunogens by, for example, enzyme-linked immunosorbent assay [see ELISA method: Published by IGAKUSHOIN (1976)].

Spleens are extracted from mice or rats whose serum exhibited sufficient antibody titer against the immunogens and then splenocytes are prepared and used as the source for antibody-producing cells.

(2) Preparation of myeloma cells

Mouse-derived established cell lines are used as a myeloma cell. For example, 8-azaguanine-resistant mouse (derived from BALB/c) myeloma cell line P3-X63Ag8-U1 (P3-U1) [Current Topics Microbiology and Immunology 81, 1–7 (1978), European J. Immunology, 6, 511–519 (1976)], SP2/O-Ag14 (SP-2) [Nature, 276, 269–270 (1978)], P3-X63-Ag8653 (653) [J. Immunology) 123, 1548–1550 (1979)] and P3-X63-Ag8 (X63) [Nature, 256, 495–497 (1975)] may be used. These cell lines may be subcultured in an 8-azaguanine medium [prepared by supplementing RPMI-1640 medium with glutamine (1.5 mM), 2-mercaptoethanol ($5\times10^{-5}$M), gentamycine (10 μg/ml) and fetal calf serum (FCS) (manufactured by CSL, 10%) (hereinafter referred to as normal medium) and further supplementing the resulting normal medium with 8-azaguanine (15 μg/ml)], and then transferred into the normal medium 3 to 4 days before cell fusion, whereby ensuring that $2\times10^7$ cells or more are obtained on the day of the cell fusion.

(3) Cell fusion

The antibody-producing cells obtained as described under (1) and the myeloma cells obtained as described under (2) are washed thoroughly with MEM medium (NISSUI SEIYAKU) or PBS (1.83 g of disodium hydrogen phosphate, 0.21 g of potassium dihydrogen phosphate, 7.65 g sodium chloride per liter of distilled water, pH 7.2), and mixed in a proportion of 5 to 10 antibody-producing cells per myeloma cell, the mixture is subjected to centrifugation (1200 rpm, 5 minutes), the supernatant is discarded and the cells which are settled are well dispersed and then admixed while stirring with the mixture containing 2 g of polyethylene glycol-1,000 (PEG-1,000), 2 ml of MEM and 0.7 ml of dimethyl sulfoxide at the rate of 0.2 to 1 ml/$10^8$ antibody-producing cells. Then, 1 to 2 ml of MEM medium is added several times at an interval of 1 to 2 minutes, and subsequently MEM medium is added so that the total volume becomes 50 ml. After centrifugation (900 rpm, 5 minutes), the supernatant is discarded and the cells are dispersed gently. Then the cells are suspended gently in 100 ml of HAT medium [prepared by supplementing the normal medium with hypoxanthine ($10^{-4}$M), thymidine ($1.5\times10^{-5}$M) and aminopterin ($4\times10^{-7}$M)] by repeated drawing up into and discharging from a graduated pipette.

This suspension is dispensed to a 96-well microplate in the volume of 200 μl/well and incubated in a 5% $CO_2$ incubator at 37° C. for 7 to 14 days.

After completion of the incubation, an aliquot of the culture supernatant is taken and screened for the wells which react specifically with the immunogen by means of, for example, the enzyme immunoassay described in section (4) below. Subsequently, cloning is repeated twice by the limiting dilution method [using HT medium (HAT medium minus aminopterine) for the 1st time and normal medium for the second time] and strains for which stable and potent antibody titer is exhibited are selected as monoclonal antibody-producing hybridoma strains.

(4) Selection of monoclonal antibody

The monoclonal antibody is selected by a binding assay using the enzyme immunoassay shown below.

From 1 to 50 μg/ml of G-CSF, ND28 or peptide fragment of ND28 conjugated with a carrier protein is dispensed to a 96-well microplate in a volume of from 10 to 100 μl/well and kept at 4° C. overnight to coat the microplate. As a control, *E. coli*-contaminated protein NY49 is coated onto the microplate similarly. After blocking with, for example, a BSA solution or the like, the hybridoma culture supernatant or the purified antibody obtained as described under (5) below is dispensed as the first antibody in a volume of 50 to 100 μl/well and reacted at room temperature for 2 hours or at 4° C. overnight. After washing with PBS or PBS supplemented with 0.5% Tween-20 (PBS-Tween), 1 to 50 μg/ml solution of anti-mouse immunoglobulin antibody labelled with biotin, an enzyme, a chemiluminescent substance, a radioactive compound or the like as the second antibody is dispensed in a volume of 50 to 100 μl/well, and reacted at room temperature for 1 to 2 hours. After thorough washing, a reaction appropriate for the label on the second antibody is conducted, whereby selecting the wells reacting specifically with the immunogen are selected.

(5) Preparation of monoclonal antibody

The monoclonal antibody-producing hybridoma cells obtained as described under (3) are intraperitoneally injected into 8 to 10 week-old nude mice treated with pristane [by intraperitoneal administration of 0.5 ml of 2,6,10,14-tetramthylpentadecane (pristane) followed by 2-week feeding] at a dose of $5\times10^6$ to $2\times10^7$ cells per animal. Within 10 to 21 days, the hybridoma becomes an ascites tumor. The ascitic fluid is collected from the mice, centrifuged (3,000 rpm, 5 minutes) to remove the solid matter, subjected to salting out using 40 to 50% saturated ammonium sulfate, and then subjected to caprylic acid precipitation to obtain a purified monoclonal antibody, or passed through a DEAR-Sepharose column, a protein A-column or a gel filtration column to collect IgG or IgM fractions, thereby obtaining a purified monoclonal antibody.

The subclass of the antibody can be determined by an enzyme immunoassay using a mouse monoclonal antibody typing kit (Zymed Laboratories) or rat monoclonal antibody typing kit (Nordic Immunology). The protein is quantified by the Lowry method and calculation from the absorbance at 280 nm.

(6) Screening of antibody A

The antiserum obtained as described under (1) or the monoclonal antibody obtained as described under (5) is examined for its reactivity with PEG-modified G-CSF and PEG-modified ND28 by means of the enzyme immunoassay. Since PEG-modified G-CSF and PEG-modified ND28 are not adsorbed onto an ELISA plate, an inhibition assay is employed. From 1 to 50 µg/ml of G-CSF, ND28 or peptide fragment of ND28 conjugated with a carrier protein is distributed in 10 to 100 µl portions into wells of a 96-well microplate and kept at 4° C. overnight to coat the wells. After blocking with, for example, BSA solution or the like, serially diluted PEG-modified G-CSF or PEG-modified ND28 is dispensed in a volume of 50 to 100 µl/well and the antiserum obtained as described under (1) or the purified antibody obtained as described under (5) is dispensed in a volume of from 50 to 100 µl/well, mixed and then reacted at room temperature for 2 hours or at 4° C. overnight. After washing with PBS or PBS supplemented with 0.05% Tween-20 (PBS-Tween), from 1 to 50 µg/ml solution of anti-mouse immunoglobulin antibody or anti-rat immunoglobulin antibody labelled with biotin, an enzyme, a chemiluminescent substance, a radioactive compound or the like as the second antibody is dispensed in a volume of 50 to 100 µl/well, and reacted at room temperature for 1 to 2 hours. After thorough washing, a reaction appropriate for the label on the second antibody is carried out. The antiserum or monoclonal antibody whose binding activity is inhibited by PEG-modified G-CSF and PEG-modified ND28 is selected as antibody A.

(7) Screening of antibody B

The monoclonal antibody obtained as described under (5) is examined for its reactivity with G-CSF, ND28, PEG-modified G-CSF and PEG-modified ND28 by enzyme immunoassay. The reactivity with PEG-modified G-CSF and PEG-modified ND28 is examined similarly as described under (6). The monoclonal antibody which reacts exclusively with G-CSF and does not react with PEG-modified G-CSF or PEG-modified ND28 is selected as antibody B.

(8) Screening of antibody C

Similarly as described under (7), the monoclonal antibody which reacts exclusively with ND28 and does not react with PEG-modified G-CSF or PEG-modified ND28 is selected as antibody C.

(9) Construction of rabbit anti-ND28 antibody

Rabbits of ages ranging from 3 to 30 weeks are immunized with ND28 or peptide fragment of ND28 conjugated with a carrier protein at a dose of 1 to 1000 µg/animal together with an appropriate adjuvant such as complete Freund's adjuvant, and then, after ensuring an elevated blood serum titer, the antiserum was taken. After salting out with 40 to 50% saturated ammonium sulfate, purification is conducted by the caprylic acid precipitation to obtain rabbit anti-ND28 antibody, or IgG fractions are collected using DEAR-Sepharose column or protein A-column to obtain rabbit anti-ND28 antibody.

The following examples are further illustrative of the invention, but are not construed to limit the scope of the invention.

EXAMPLE 1

(1) Immunization of Animals and Preparation of Antibody-producing Cells

Balb/c female mice 8 weeks of age were immunized with G-CSF produced by $E.\ coli$ using recombinant DNA technology, ND28 produced by $E.\ coli$ or peptide fragments of ND28. For the purpose of enhancing the immunogenicity, the peptide fragments of ND28 are conjugated with KLH (CALBIOCHEM) using m-maleimidebenzoyl-N-hydroxysuccyl (MBS, Nakalai Tesque) as a crosslinking agent to obtain an immunogen. For the reaction with MBS, peptide was synthesized with adding Cys to the N-terminal. The method of preparing an immunogen is shown below.

KLH was dissolved in BPS at a concentration of 10 mg/ml, a tenth of the volume of 25 mg/ml MBS was added dropwise and the mixture was reacted at room temperature for 30 minutes with stirring. Free MBS was removed on a Sephadex G-25 column which had previously been equilibrated with PBS to yield 2.5 mg of KHL-MBS, which was then admixed with 1 mg of peptide dissolved in 0.1M sodium phosphate buffer (pH 7.9) and reacted at room temperature for 3 hours with stirring. After the reaction, an immunogen was obtained by dialysis against PBS containing 0.5M sodium chloride.

Balb/c female mice 8 weeks of age were given 100 µg of the immunogen together with 2 mg of aluminum gel and $1\times10^9$ cells of pertussis vaccine (Chiba Serum Research Center) in the first administration. After 2 weeks, weekly administration of 100 µg of the immunogen was started. After 4 administrations in all, blood was sampled from the venous plexus of the fundus of the eye, and the serum antibody titre was determined by the enzyme immunoassay described below.

From the mice which exhibited sufficient increase in antibody titre against the immunogen, spleens were excised 3 days after the final immunization. The spleens were cut into pieces in MEM medium (Nissui Phamaceutical), and disintegrated using a forceps. After centrifugation (1200 rpm, 5 minutes), the supernatant was discarded and the erythrocytes were removed by treatment with Tris-ammonium chloride buffer (pH 7.65) for 1 to 2 minutes. The cells were then washed three times with MEM medium and submitted for cell fusion.

Enzyme Immunoassay (Bindinq Assay)

Into wells of a 96-well plate for EIA (GREINER), 10 µg/ml of G-CSF, ND28, ND28 peptide fragment-thyroglobulin (THY) conjugate, $E.\ coli$ contaminant protein NY49 as a negative antigen or peptide-THY conjugate other than the antigen was dispensed in a volume of 50 µl/well and the plate was kept overnight to achieve adsorption. ND28 peptide fragment-THY conjugate was prepared by a glutaraldehyde method. Thus, 1 mg of the peptide was dissolved in 0.1M ammonium acetate buffer (pH 7.0) and 5 mg of THY dissolved in the same buffer solution was added to make the total volume 1 ml. Then, 540 µl of 0.02M glutaraldehyde were added dropwise with stirring and reacted at room temperature for 5 hours with stirring. After the reaction followed by dialysis against PBS overnight, ND28 peptide fragment-THY conjugate was obtained.

After washing the plate, PBS solution containing 1% BSA (BSA-PBS) was dispensed in a volume of 100 µl/well and kept at room temperature for 1 hour or at 4° C. overnight for blocking the protein binding residues remaining on the plate. After discarding BSA-PBS and washing thoroughly with PBS, samples (mouse serum, hybridoma culture supernatant, purified monoclonal antibody) diluted with BSA-PBS were dispensed as the first antibody in a volume of 50 μl/well and kept at room temperature for 2 hours or at 4° C. overnight. After thorough washing with PBS-Tween, peroxidase-labelled anti-mouse immunoglobulin antibody (DAKO) was dispensed as the second antibody in the volume of 50 μl/well and kept at room temperature for 1 hour. After thorough washing with PBS-Tween, color was developed using ABTS substrate solution [prepared by dissolving 550 mg of 2,2'-azinobis(3-ethylbenzothiazolin-6-sulfonic acid) diammonium salt in 1L of 0.1M citrate buffer (pH 4.2) and supplementing just prior to use with 1 μl/ml of hydrogen peroxide] and absorbance at $OD_{415nm}$ was determined.

(2) Preparation of Mouse Myeloma Cells 8-azaguanine-resistant mouse myeloma cell line P3-U1 was cultivated in normal medium and harvested in an amount of $2 \times 10^7$ or more at the time of cell fusion, where it was used as a parent cell line.

(3) Preparation of Hybridoma

The mouse splenocytes obtained in Example 1-(1) and the myeloma cells obtained in Example 1-(2) were mixed in the ratio of 10:1. After the mixture was centrifuged (1200 rpm, 5 minutes), the supernatant was discarded and the cells which settled were throughly loosened and then, with stirring, the mixture containing 2 g of polyethylene glycol-1,000 (PEG-1,000), 2 ml of MEM and 0.7 ml of dimethyl sulfoxide were added at 37° C. to the cells in an amount of 0.2 to 1 ml/$10^8$ mouse splenocytes. Then from 1 to 2 ml of MEM medium was added several times at an interval of 1 to 2 minutes, and subsequently MEM medium was added so that the total volume became 50 ml. After centrifugation (900 rpm, 5 minutes), the supernatant was discarded and the cells were loosened gently. Then, the cells were suspended gently in 100 ml of HAT medium by repeated drawing up into and discharging from a graduated pipette.

The suspension was dispensed into wells of a 96-well microplate at a volume of 200 μl/well and incubated in a 5% $CO_2$ incubator at 37° C. for 10 to 14 days. The cultivated supernatant was selected from the wells which react specifically with the immunogen by the enzyme immunoassay described in Example 1-(1) above. Subsequently, cloning was repeated twice using HT medium and normal medium to obtain a hybridoma strain.

As shown in FIG. 1, hybridoma KM341, KM342, KM509 and KM510 were selected as the hybridomas producing the monoclonal antibodies which reacted with G-CSF and ND28, KM343 as the hybridoma producing the monoclonal antibody which reacted with G-CSF but not with ND28, and KM498 and KM511 as the hybridomas producing the monoclonal antibody which reacted with ND28 but not with G-CSF.

(4) Purification of Monoclonal Antibody

The hybridoma strains obtained in Example 1-(3) were respectively administered to pristane-treated nude mice 8 weeks of age by intraperitoneal injection at a dose of 5 to $20 \times 10^6$ cells/animal. Within 10 to 21 days, the hybridoma became an ascitic tumor. The ascites fluid was taken from each ascitic fluid-carrying mouse (1 to 8 ml/animal) and centrifuged (3000 rpm, 5 minutes) to remove solid matter. In the case of a monoclonal antibody of the class IgM, the supernatant was subjected to salting out with 50% ammonium sulfate, followed by dialysis against PBS supplemented with 0.5 M sodium chloride, followed by passing through Cellulofine GSL 2000 (SEIKAGAKU CORP.) column (bed volume: 750 ml) at a flow rate of 15 ml/hour thereby collecting IgM fraction as the purified monoclonal antibody. In the case of a monoclonal antibody of the class IgG, the supernatant was purified by a caprylic acid precipitation method (Antibodies-A Laboratory Manual, Cold Spring Harbor Laboratory, 1988), whereby a purified monoclonal antibody was obtained.

The subclasses of the antibodies were determined by enzyme immunoassay using a subclass typing kit. The subclasses of the hybridomas obtained in Example 1-(3) are shown in Table 2.

TABLE 2

| Monoclonal Antibody | KM341 | KM342 | KM343 | KM498 | KM509 | KM510 | KM511 |
| --- | --- | --- | --- | --- | --- | --- | --- |
| Subclass | G1 | G1 | G1 | G1 | G2a | G1 | G1 |

(5) Study of the Reactivity with PEG-modified G-CSF and PEG-modified ND28

The reactivity of the monoclonal antibody produced by the hybridoma obtained in Example 1-(4) with PEG-modified G-CSF and PEG-modified ND28 was examined by the inhibition assay using the enzyme immunoassay as described below. The molecular weight of PEG which constituted PEG-modified G-CSF and PEG-modified ND28 was about 10,000, and 3 molecules of PEG were bound to each molecule of G-CSF or ND28.

Figure 1A:
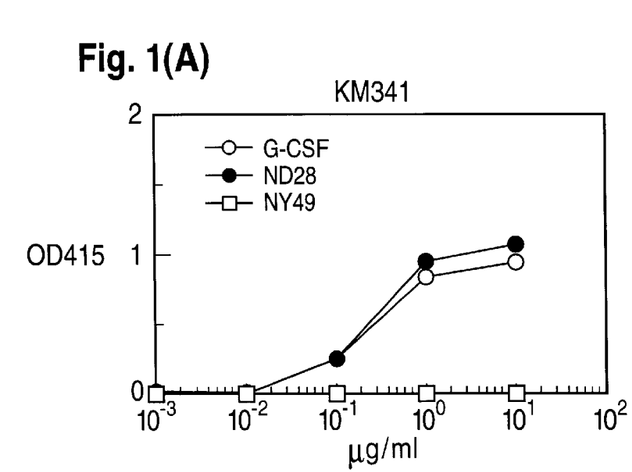
FIGS. 1(A), 1(B), 1(C), 1(D), 1(E), 1(F) and 1(G) show the reactivity of monoclonal antibodies KM341, KM342, KM343, KM498, KM509, KM510 and KM511, respectively with G-CSF, ND28 and E. coli-derived contaminant protein NY49 using a binding assay.
Figure 1B:
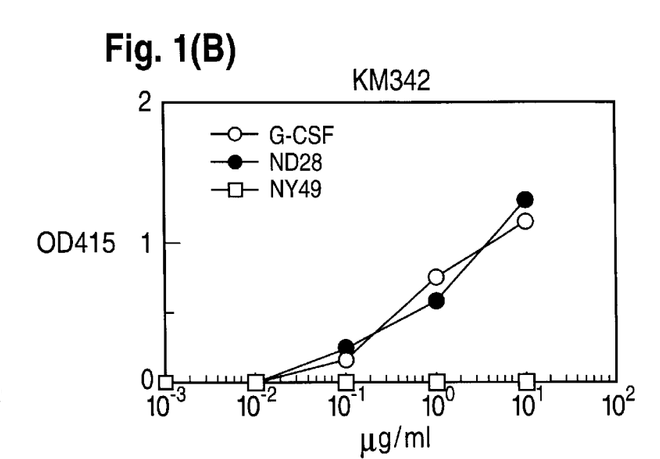
Figure 1C:
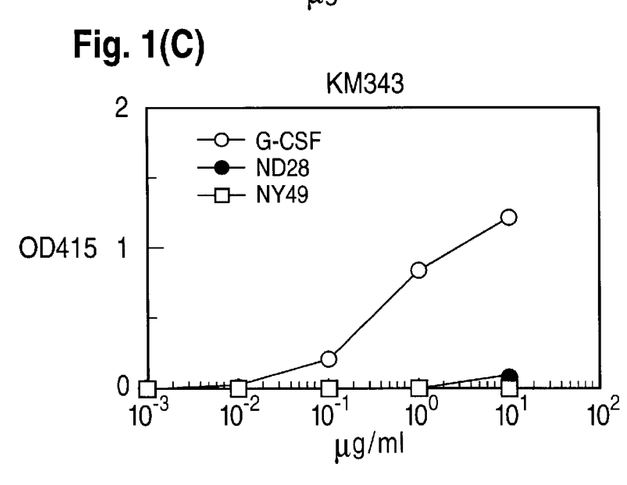
Figure 1D:
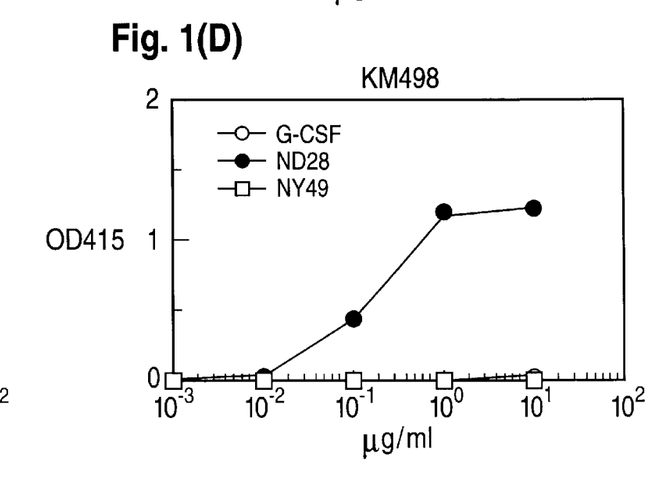
Figure 1E:
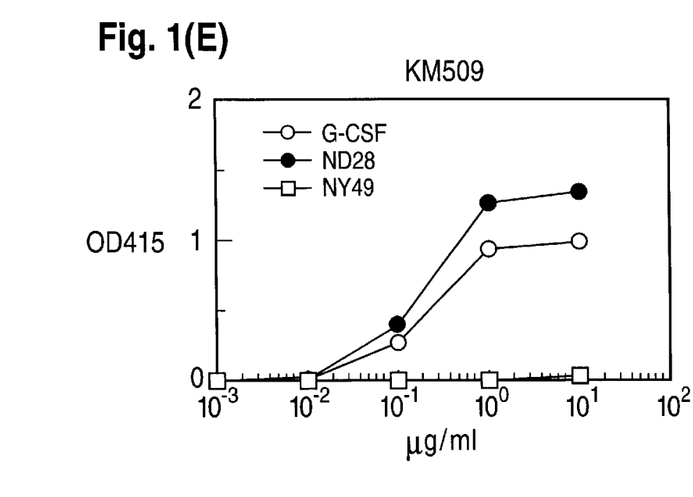
Figure 1F:
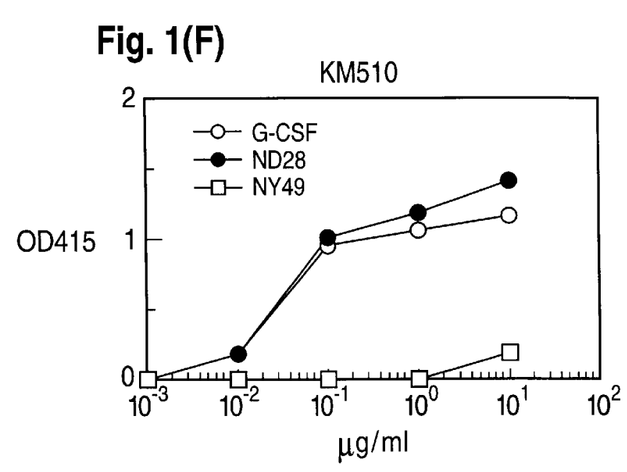
Figure 1G:
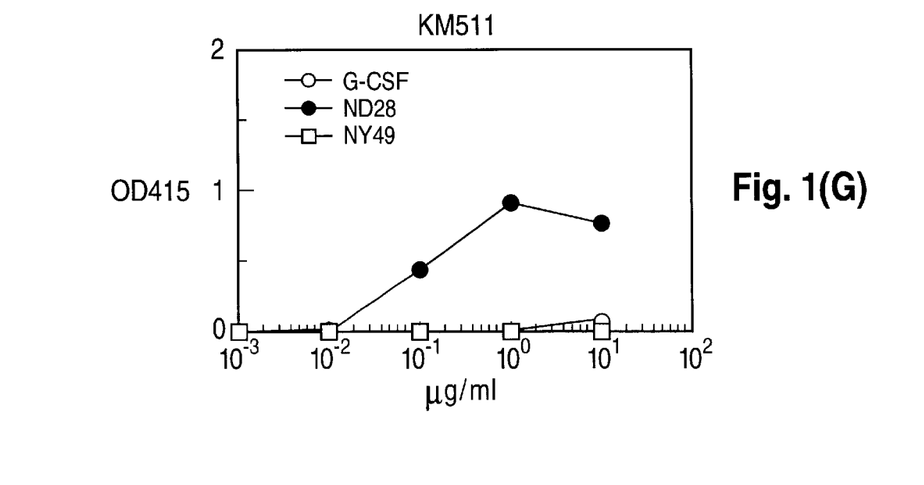
Figure 2A:
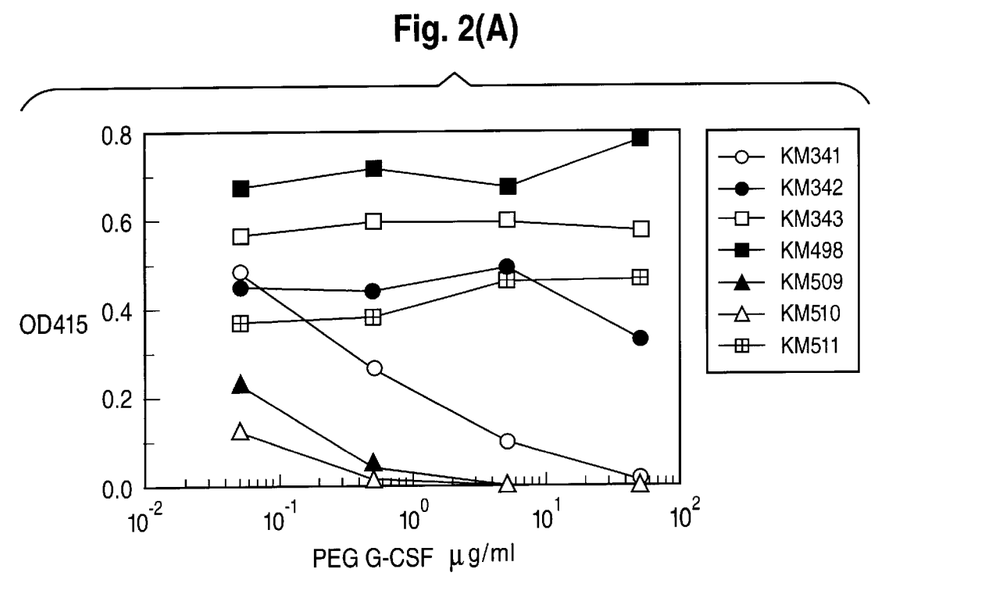
FIGS. 2(A) and 2(B) show the reactivity of monoclonal antibodies KM341, KM342, KM343, KM498, KM509, KM510 and KM511 with PEG-modified G-CSF (A) and with PEG-modified ND28 (B) using an inhibition assay.
Figure 2B:
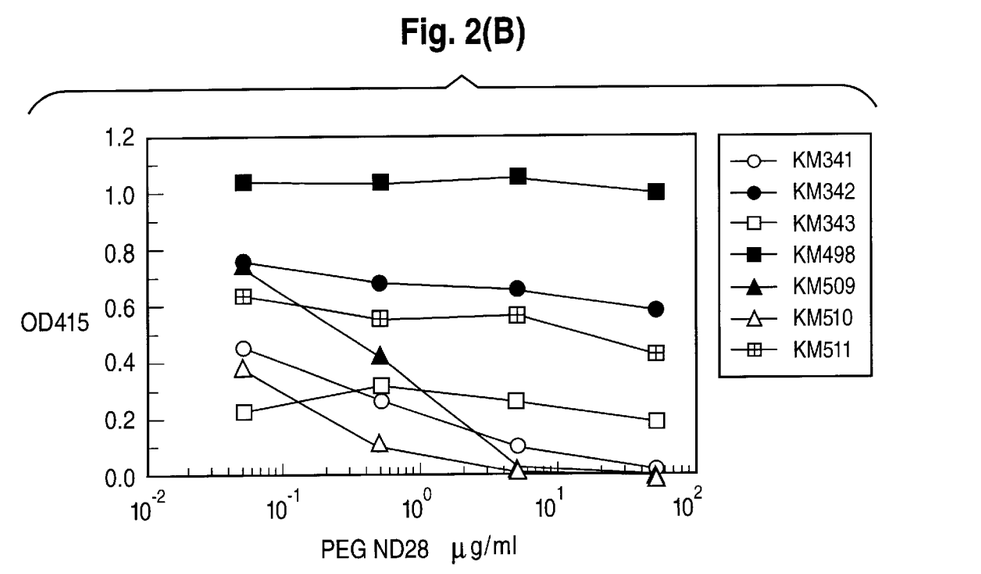

10 μg/ml of each immunogen was dispensed to a 96-well microplate in a volume of 50 μl/well and kept at 4° C. to coat the plate, which was then blocked with BSA-PBS. Serially diluted PEG-modified G-CSF or PEG-modified ND28 at a concentration of 100 μg/ml to 0.1 μg/ml was dispensed in a volume of 50 μl/well, and the purified antibody obtained in Example 1-(4) was dispensed in a volume of 50 μl/well, mixed, and then reacted at room temperature for 2 hours. After washing thoroughly with PBS-Tween, peroxidase-labelled anti-mouse immunoglobulin antibody (produced by DAKO) was dispensed in a volume of 50 μl/well, and kept at room temperature for 1 hour. After washing thoroughly with PBS-Tween, color was developed similarly as in Example 1-(1) and absorbance at $OD_{415nm}$ was measured. As shown in FIG. 2, the binding activity of monoclonal antibodies KM341, KM509 and KM510 produced by hybridoma KM341, KM509 and KM510, respectively, which were included in the hybridomas selected in Example 1-(3), was inhibited by PEG-modified G-CSF and PEG-modified ND28 in a dose-dependent manner, indicating these monoclonal antibodies react with PEG-modified G-CSF and PEG-modified ND28.

(6) Construction of Rabbit Anti-ND28 Antibody

Figure 3A:
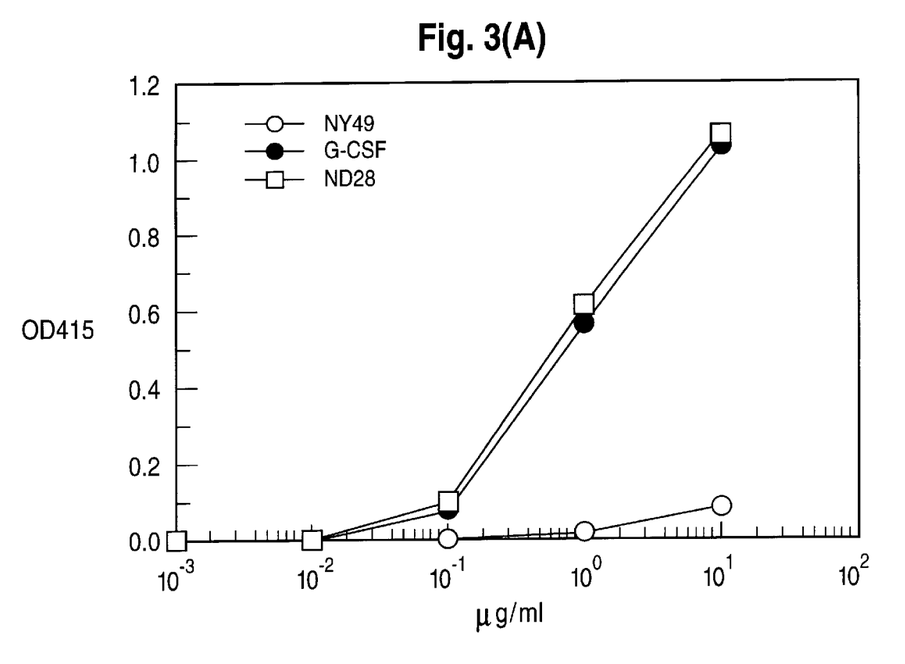
FIGS. 3(A) and 3(B) show the reactivity of the rabbit anti-ND28 antibody with G-CSF, ND28 and E. coli-derived contaminant protein NY49 (A) in a binding assay and with PEG-modified ND28 (B) in an inhibition assay.
Figure 3B:
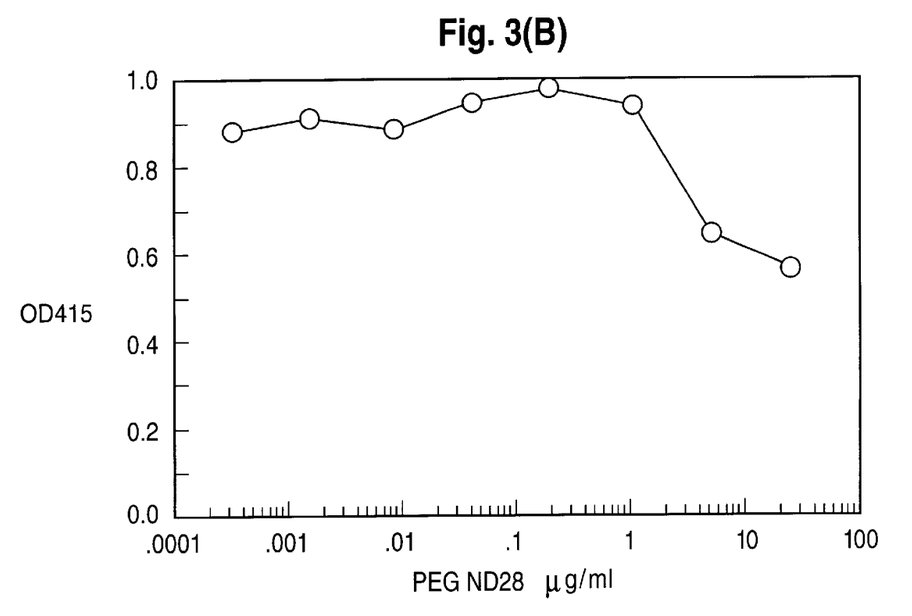

100 μg/animal of ND28 produced by E.coli by means of recombinant DNA engineering were administered subcutaneously 4 times at the interval of 1 week together with complete Freund's adjuvant (Nakalai Tesque), and then 1000 μg/animal of ND28 were administered 6 times at an interval of 2 weeks together with incomplete Freund adjuvant. After determining an elevated blood antibody titer by enzyme immunoassay, the antiserum was taken. By means of a caprylic acid precipitation method and salting out using 50% saturated ammonium sulfate, an IgG fraction was collected as the rabbit anti-ND28 antibody. FIG. 3 shows the reactivity of the rabbit anti-ND28 antibody with ND28, G-CSF and PEG-modified ND28.

(7) Establishment of Quantification System for G-CSF, ND28, PEG-modified G-CSF and PEG-modified ND28 Using Monoclonal Antibody Reacting with PEG-modified G-CSF and PEG-modified ND28

Figure 4:
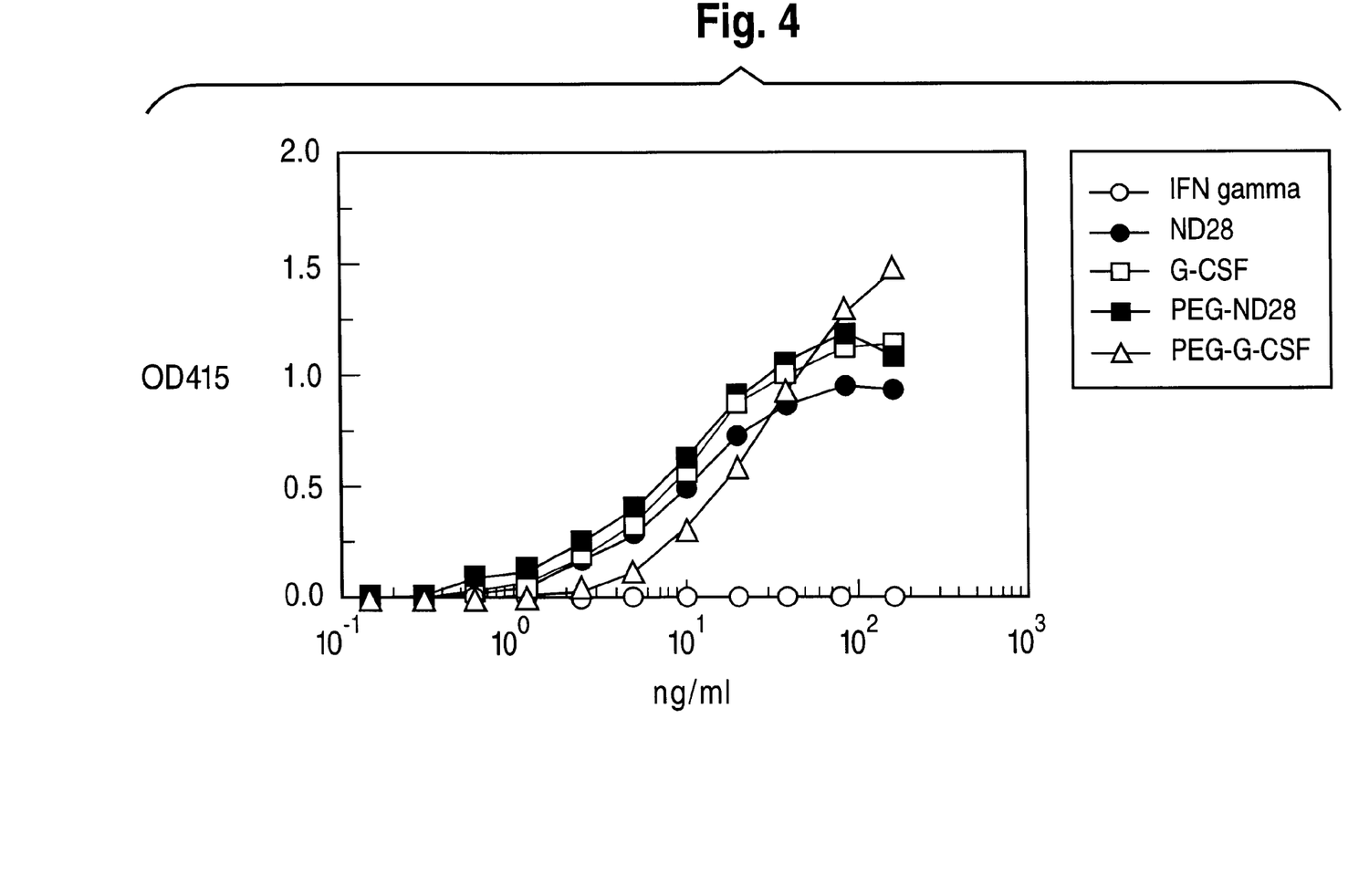
FIG. 4 shows the quantification curves of G-CSF, ND28, PEG-modified G-CSF, PEG-modified ND28 and interferon γ by sandwich ELISA using KM509 as the first antibody and biotin-labelled rabbit anti-ND28 as the second antibody.

Using the monoclonal antibody reacting with PEG-modified G-CSF and PEG-modified ND28 selected in Example 1-(5) and the rabbit anti-ND28 antibody constructed in Example 1-(6), a quantification system for PEG-modified ND28 by the sandwich ELISA method was examined. Then, 10 μg/ml of the monoclonal antibody reacting with PEG-modified G-CSF and PEG-modified ND28 or the rabbit anti-ND28 antibody were dispensed as the first antibody in a volume of 50 μl/well into a 96-well microplate, which was kept at 4° C. overnight to coat the plate. After blocking with BSA solution, PEG-modified ND28, which had been subjected to a 2-fold serial dilution to a concentration within the range from 160 ng/ml to 0.15625 ng/ml, was dispensed at a volume of 50 μl/well and reacted at 4° C. overnight. After washing, 10 μg/ml of biotin-labelled monoclonal antibody reacting with PEG-modified G-CSF and PEG-modified ND28 or rabbit anti-ND28 antibody was dispensed at a volume of 50 μl/well and reacted at room temperature for 1 to 2 hours. After thorough washing, avidin-peroxidase (produced by VECTOR) was dispensed in a volume of 50 μl/well, and reacted at room temperature for from 1 to 2 hours. After thorough washing with PBS-Tween, color was developed similarly as in Example 1-(1) and the absorbance at $OD_{415nm}$ was measured. Among 16 combinations of the first antibodies with the second antibodies, the combination of KM509 as the first antibody and the rabbit anti-ND28 antibody as the second antibody was selected as the combination by which PEG-modified ND28 could be detected at the highest sensitivity. The system employing this combination provided the quantification curves for G-CSF, ND28, PEG-modified G-CSF, PEG-modified ND28 and interferon γ as shown in FIG. 4. As evident from FIG. 4, this system was able to detect ND28, G-CSF, PEG-modified G-CSF and PEG-modified ND28 at the same sensitivity.

Figure 5:
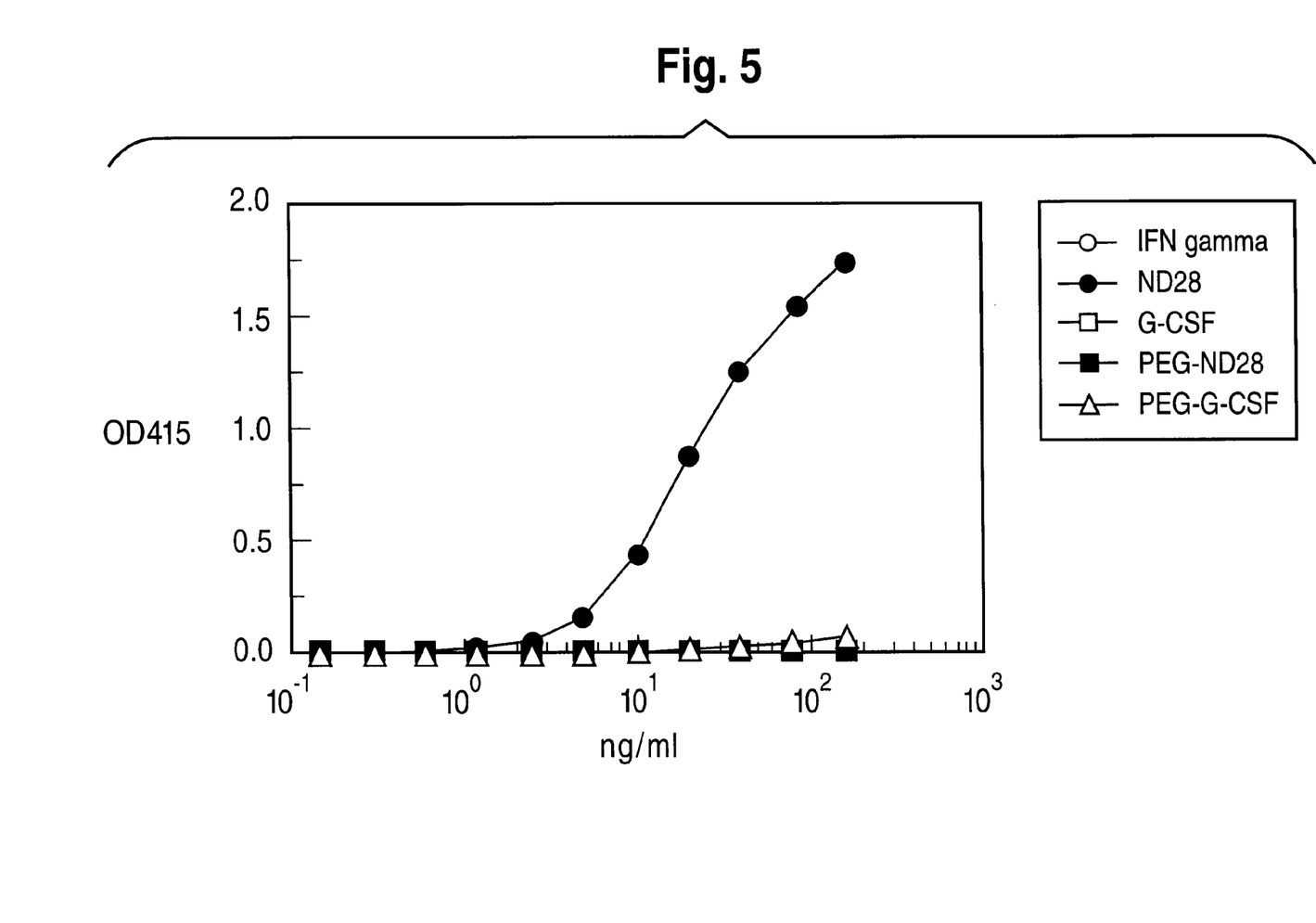
FIG. 5 shows the quantification curves of G-CSF, ND28, PEG-modified G-CSF, PEG-modified ND28 and interferon γ by by sandwich ELISA using KM511 as the first antibody and biotin-labelled rabbit anti-ND28 as the second antibody.

(8) Establishment of Quantification System for ND28 using Anti-ND28 Monoclonal Antibody From the monoclonal antibodies produced by the hybridomas obtained in Example 1-(3), KM498 or KM511, which reacted with ND28 but not with G-CSF, PEG-modified G-CSF or PEG-modified ND28, was used as the first antibody, and the rabbit anti-ND28 antibody constructed in Example 1-(6) was used as the second antibody to examine the quantification system specific to ND28 by the sandwich ELISA. As a result, the combination of KM511 as the first antibody with the rabbit anti-ND28 antibody as the second antibody was selected. The system employing this combination provided the quantification curves for G-CSF, ND28, PEG-modified G-CSF, PEG-modified ND28 and interferon γ as shown in FIG. 5. As is evident from FIG. 5, this quantification system was able to detect ND28 specifically.

Figure 6:
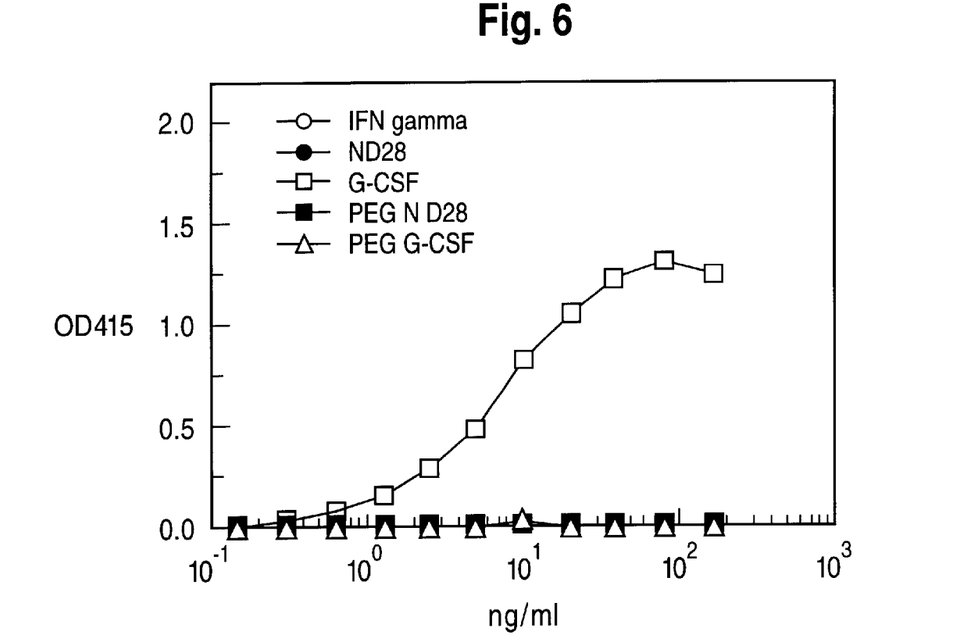
FIG. 6 shows the quantification curves of G-CSF, ND28, PEG-modified G-CSF, PEG-modified ND28 and interferon γ by sandwich ELISA using KM343 as the first antibody and biotin-labelled rabbit anti-ND28 as the second antibody.

(9) Establishment of Quantification System for G-CSF Using Anti-G-CSF Monoclonal Antibody From the monoclonal antibodies produced by the hybridomas obtained in Example 1-(3), KM343, which reacted with G-CSF, but not with ND28, PEG-modified G-CSF or PEG-modified ND28, was used as the first antibody, and the rabbit anti-ND28 antibody constructed in Example 1-(6) was used as the second antibody to establish the quantification system specific to G-CSF by the sandwich ELISA. This quantification system provided the quantification curves for G-CSF, ND28, PEG-modified G-CSF, PEG-modified ND28 and interferon γ as shown in FIG. 6. As is evident from FIG. 6, this quantification system was able to detect G-CSF specifically.

(10) Quantification of PEG-modified ND28

By subtracting the value obtained by the quantification system specific to ND28 established in Example 1-(8) and the value obtained by the quantification system specific to G-CSF established in Eample 1-(9) from the value obtained by quantification system established in Example 1-(7), PEG-modified ND28 could be quantified at a high sensitivity.

EXAMPLE 2

(1) Establishment of PEG-modified ND28 and ND28 using Anti-ND28 Antibody (Quantification System 1)

From the anti-ND28 antibody obtained in Example 1-(6), peroxidase-labelled rabbit anti-ND28 antibody Fab' was constructed by hinge method [Enzyme immunoassay, 3rd Ed., IGAKUSHOIN).

Figure 7:
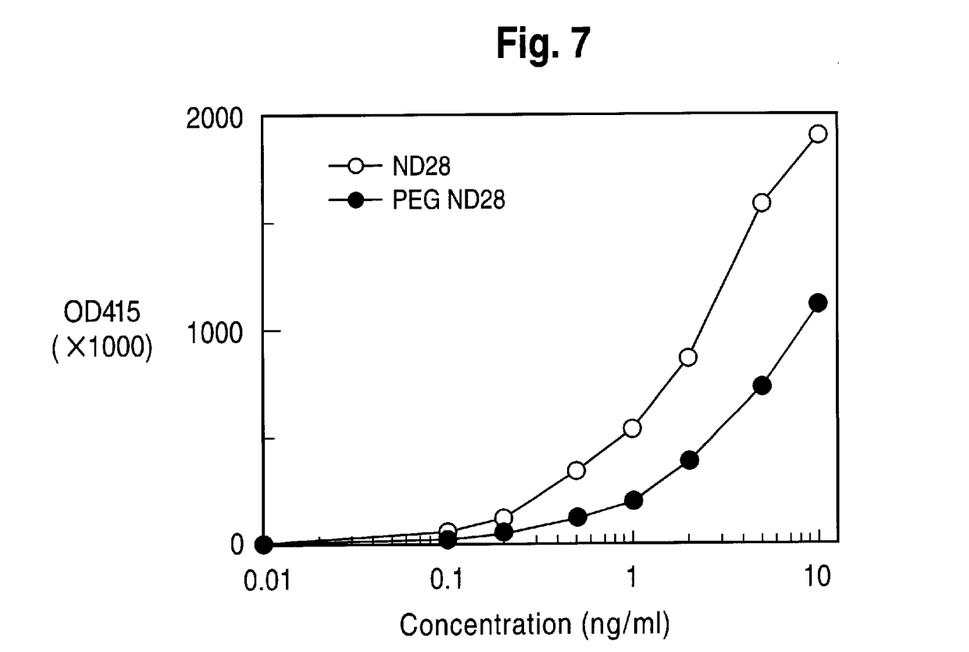
FIG. 7 shows the quantification curves of ND28 and PEG-modified ND28 by sandwich ELISA using the rabbit anti-ND28 antibody as the first antibody and peroxidase-labelled rabbit anti-ND28 Fab' as the second antibody.

Using the rabbit anti-ND28 antibody as the first antibody and the peroxidase-labelled rabbit anti-ND28 antibody Fab' as the second antibody, a quantification system for PEG-modified ND28 and ND28 by the sandwich ELISA was established. The quantification curves of PEG-modified ND28 and ND28 by this quantification system are shown in FIG. 7. As is evident from FIG. 7, this quantification system was able to quantify ND28 and PEG-modified ND28.

(2) Establishment of Quantification System for ND28

Figure 8:
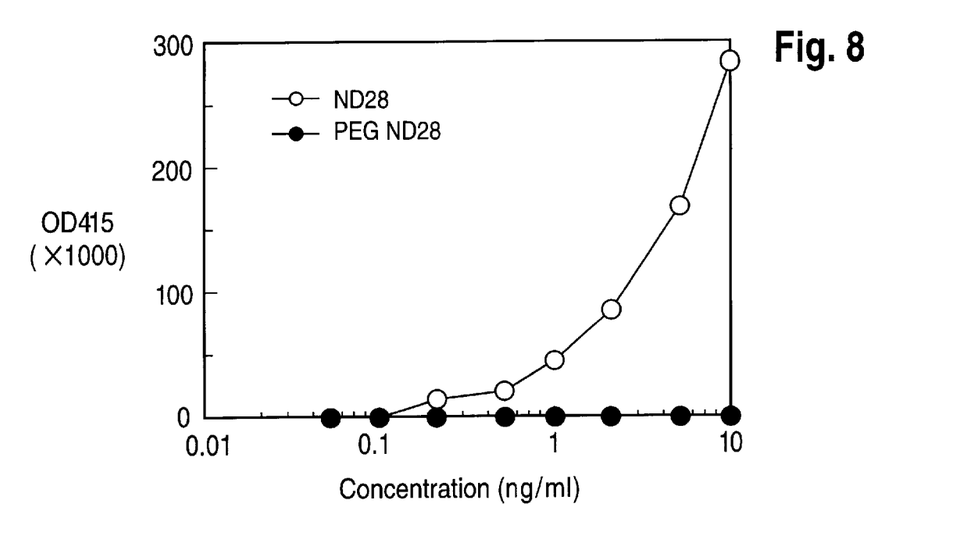
FIG. 8 shows the quantification curves of ND28 and PEG-modified ND28 by sandwich ELISA using KM511 as the first antibody and peroxidase-labelled rabbit anti-ND28 as the second antibody.

Using KM511, which is a monoclonal antibody which reacts with ND28 but not with G-CSF, PEG-modified G-CSF or PEG-modified ND28, as the first antibody and the peroxidase-labelled rabbit anti-ND28 antibody as the second antibody, the quantification system for ND28 by the sandwich ELISA was established. The quantification curves of PEG-modified ND28 and ND28 by this quantification system are shown in FIG. 8. As is evident from FIG. 8, this quantification system was able to quantify ND28.

(3) Quantification of PEG-modified ND28

Similar to Example 1, by subtracting the value obtained by the quantification system specific to ND28 established in Example 2-(2) from the value obtained by quantification system for ND28 and PEG-modified ND28 established in Example 2-(1), PEG-modified ND28 could be quantified at a high sensitivity.

EXAMPLE 3

Quantification of PEG-modified ND26 in the Blood of Rats Treated with PEG-modified ND28

Figure 9:
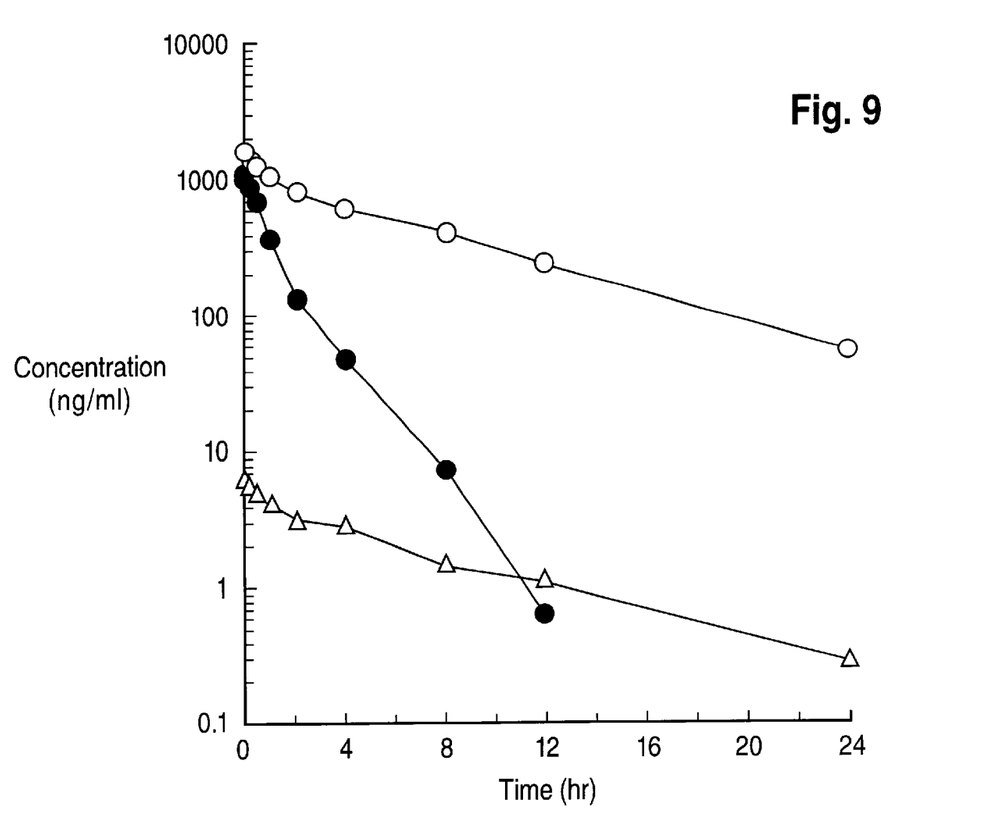
FIG. 9 shows the results of the quantification of PEG-modified ND28 and ND28 in blood samples collected at various time intervals from rats treated with PEG-modified ND28 and ND28. ○ represents the PEG-modified ND28 and ND28 in the blood of rats treated with PEG-modified ND28, Δ represents ND28 in the blood of rats treated with PEG-modified ND28, and ● represents ND28 in the blood of rats treated with ND28.

Using the quantification system established in Example 2-(3), PEG-modified ND28 in the blood of rats treated with PEG-modified modified ND28 was determined. In addition, using the quantification system established in Example 2-(2), ND28 in the blood of rats treated with ND28 was determined. 50 μg/kg body weight of PEG-modified ND28 or ND28 was administered intravenously to rats, and then the serum was taken at the indicated time intervals to determine serum PEG-modified ND28 or serum ND28. The results are shown in FIG. 9. As is evident from FIG. 9, PEG-modified ND28 exhibited the blood clearance which was reduced significantly when compared with ND28.

While the invention has been described in detail and with reference to specific examples thereof, it will be apparent to one skilled in the art that various changes and modifications can be made therein without departing from the spirit and scope thereof.

What is claimed is:

1. An immunological assay for quantifying PEG-modified human granulocyte colony stimulating factor (G-CSF) or derivatives as shown in table 1 in a sample, said assay comprising the steps of:
   (1) contacting said sample with a first antibody which specifically binds to the human G-CSF or its derivative and PEG-modified human G-CSF or its derivative under conditions where said first antibody binds to the human G-CSF or its derivative and the PEG-modified human G-CSF or its derivative, to form a first mixture;
   (2) adding a labeled second antibody to said first mixture, which specifically binds to the human G-CSF or its derivative and the PEG-modified human G-CSF or its derivative, under conditions where binding occurs to form a second mixture;
   (3) detecting said labeled second antibody bound to the human G-CSF or its derivative and the PEG-modified human G-CSF or its derivative in said second mixture;
   (4) quantifying the amount of the human G-CSF or its derivative and the PEG-modified human G-CSF or its derivative in said second mixture from said detecting said labeled second antibody;
   (5) contacting said sample with a third antibody, wherein said antibody is a monoclonal antibody which binds specifically to the G-CSF or its derivative but does not bind specifically with the PEG-modified human G-CSF or its derivative under conditions where said third antibody binds said G-CSF or its derivative, to form a third mixture;
   (6) adding a labeled fourth antibody, wherein said antibody is a monoclonal antibody to said third mixture which specifically binds the human G-CSF or its derivative but does not bind specifically with the PEG-modified human G-CSF or its derivative under conditions where binding occurs to form a fourth mixture;
   (7) detecting said labeled fourth antibody bound to the human G-CSF or its derivative in said fourth mixture;
   (8) quantifying the amount of said G-CSF or its derivative in said fourth mixture from said detecting said labeled fourth antibody;
   (9) subtracting the value obtained by quantifying G-CSF or its derivative from the value obtained by quantifying G-CSF or its derivative and PEG-modified G-CSF or its derivative; and
   (10) determining the amount of PEG-modified G-CSF or its derivative from said subtracting.

2. The immunological assay according to claim 1 wherein the first antibody is a polyclonal antibody.

3. The immunological assay according to claim 1 wherein the first antibody is a monoclonal antibody.

4. The immunological assay according to claim 1 wherein the first antibody is a monoclonal antibody produced by hybridoma KM509 (FERM BP-4774).

5. The immunological assay according to claim 1 wherein the human granulocyte colony stimulating factor derivative is human granulocyte colony stimulating factor derivative ND28.

6. The immunological assay according to claim 1 wherein the immunological assay is an enzyme solid-phase sandwich immunoassay.

7. The immunological assay of claim 1 wherein said monoclonal antibody of step (5) is a monoclonal antibody which is produced by hybridoma KM343 (FERM BP-4879) and which binds specifically to human granulocyte colony stimulating factor but not with human granulocyte colony stimulating factor derivative ND 28, PEG-modified human granulocyte colony stimulating factor or PEG-modified human granulocyte colony stimulating factor derivative ND 28.

8. The immunological assay of claim 1 wherein said monoclonal antibody of step (5) is a monoclonal antibody which is produced by hybridoma KM511 (FERM BP-4880) and which binds specifically to human granulocyte colony stimulating factor derivative ND 28 but not with human granulocyte colony stimulating factor, PEG-modified human granulocyte colony stimulating factor or PEG-modified human granulocyte colony stimulating factor derivative ND 28.

9. A monoclonal antibody which is produced by hybridoma KM509 (FERM BP-4774) and which binds to human granulocyte colony stimulating factor, human granulocyte colony stimulating factor derivative ND28, PEG-modified human granulocyte colony simulating factor and PEG-modified human granulocyte colony stimulating factor derivative ND 28.

* * * * *